US012702362B2

(12) United States Patent
Singleton et al.

(10) Patent No.: US 12,702,362 B2
(45) Date of Patent: Aug. 11, 2026

(54) MEASURING IMPACT OF ENVIRONMENTAL FACTORS ON PHYSIOLOGICAL DATA COLLECTED FROM A WEARABLE

(71) Applicant: Oura Health Oy, Oulu (FI)

(72) Inventors: Robert Alexander Singleton, Toronto (CA); Mari Pauliina Karsikas, Oulu (FI); Johanna Leena Kyllikki Still, Oulu (FI); Miska Mikael Viljami Valkonen, Jyväskylä (FI)

(73) Assignee: Oura Health Oy, Oulu (FI)

( * ) Notice: Subject to any disclaimer, the term of this patent is extended or adjusted under 35 U.S.C. 154(b) by 374 days.

(21) Appl. No.: 18/324,893

(22) Filed: May 26, 2023

(65) Prior Publication Data

US 2023/0380776 A1 Nov. 30, 2023

Related U.S. Application Data

(60) Provisional application No. 63/347,099, filed on May 31, 2022.

(51) Int. Cl.
*A61B 5/00* (2006.01)

(52) U.S. Cl.
CPC ............ *A61B 5/7475* (2013.01); *A61B 5/486* (2013.01); *A61B 5/6802* (2013.01); *A61B 2560/0242* (2013.01)

(58) Field of Classification Search
None
See application file for complete search history.

(56) References Cited

U.S. PATENT DOCUMENTS 8,157,730 B2 * 4/2012 LeBoeuf ................ G16H 10/60 600/595
11,701,023 B1 * 7/2023 Davis ..................... A61B 5/053 600/547

(Continued)

OTHER PUBLICATIONS

Cheong et al. Sensing Physiological Change and Mental Stress in Older Adults from Hot Weather, IEEE Access vol. 8 2020, publication Mar. 20, 2020.*

(Continued)

*Primary Examiner* — David J Stoltenberg
(74) *Attorney, Agent, or Firm* — ArentFox Schiff LLP

(57) ABSTRACT

Methods, systems, and devices for emotional well-being correlation are described. A system may receive physiological data associated with a user from a wearable device worn by the user, environmental data including characteristics of an environment of the user, and feedback data from the user indicating a physical state or a psychological state of the user when experiencing the at least one environmental characteristic. The system may additionally determine a set of relationships between the received environmental data and the received feedback data, the received physiological data, or both. Additionally, the system may generate a message for the user based on the set of relationships and display the message to the user via a graphical user interface (GUI) of a user device. The message may include instructions for regulating the physical state of the user, the psychological state of the user, or both, when experiencing the characteristics of the environment.

20 Claims, 9 Drawing Sheets

(56) References Cited

U.S. PATENT DOCUMENTS

| | | | | |
|---|---|---|---|---|
| 12,125,398 | B1 * | 10/2024 | Cohn | G16H 10/60 |
| 2005/0148828 | A1 * | 7/2005 | Lindsay | A61B 5/00 128/920 |
| 2011/0098112 | A1 * | 4/2011 | LeBoeuf | A61B 5/0002 463/31 |
| 2012/0289793 | A1 * | 11/2012 | Jain | G16Z 99/00 600/301 |
| 2017/0000416 | A1 * | 1/2017 | EhrenKranz | G08B 21/0453 |
| 2017/0189751 | A1 * | 7/2017 | Knickerbocker | A61B 5/1114 |
| 2018/0189375 | A1 * | 7/2018 | Gibson | G16H 40/63 |
| 2018/0322950 | A1 * | 11/2018 | Cronin | A61B 5/026 |
| 2020/0345300 | A1 * | 11/2020 | Potyrailo | G16H 20/70 |
| 2021/0170232 | A1 * | 6/2021 | Kabbash | A61B 5/1122 |
| 2021/0345912 | A1 * | 11/2021 | Zakharov | A61B 3/113 |
| 2022/0079521 | A1 * | 3/2022 | Grena | G01J 1/42 |
| 2022/0157145 | A1 * | 5/2022 | Panneer Selvam | A61B 5/0002 |
| 2024/0008784 | A1 * | 1/2024 | Ehsani | A61B 5/7267 |
| 2025/0040830 | A1 * | 2/2025 | Weydert | A61B 5/486 |

OTHER PUBLICATIONS

Sheikh et al., Wearable, Environmental, and Smartphone-Based Passive Sensing for Mental Health Monitoring, Frontiers in Digital Health www.frontiersin.org Apr. 2021 olume 3 | Article 662811.*

Rodrigues et al. Physiological and Behavior Monitoring Systems for Smart Healthcare Environments: A Review; Sensors 2020, 20, 2186; doi:10.3390/s20082186.*

* cited by examiner

MEASURING IMPACT OF ENVIRONMENTAL FACTORS ON PHYSIOLOGICAL DATA COLLECTED FROM A WEARABLE

CROSS REFERENCE

The present application for patent claims the benefit of U.S. Provisional Patent Application No. 63/347,099 by SINGLETON et al., entitled "IMPACTS OF WEATHER ON EMOTIONAL WELL-BEING," filed May 31, 2022, assigned to the assignee hereof, and expressly incorporated by reference herein.

FIELD OF TECHNOLOGY

The following relates to wearable devices and data processing, including measuring impact of environmental factors on physiological data collected from a wearable.

BACKGROUND

Some wearable devices may be configured to collect data from users. For example, a wearable device may include one or more sensors that collect physiological data from a user. Some systems associated with the wearable devices may also be able to provide certain health insights to users.

DETAILED DESCRIPTION

Figure 1:
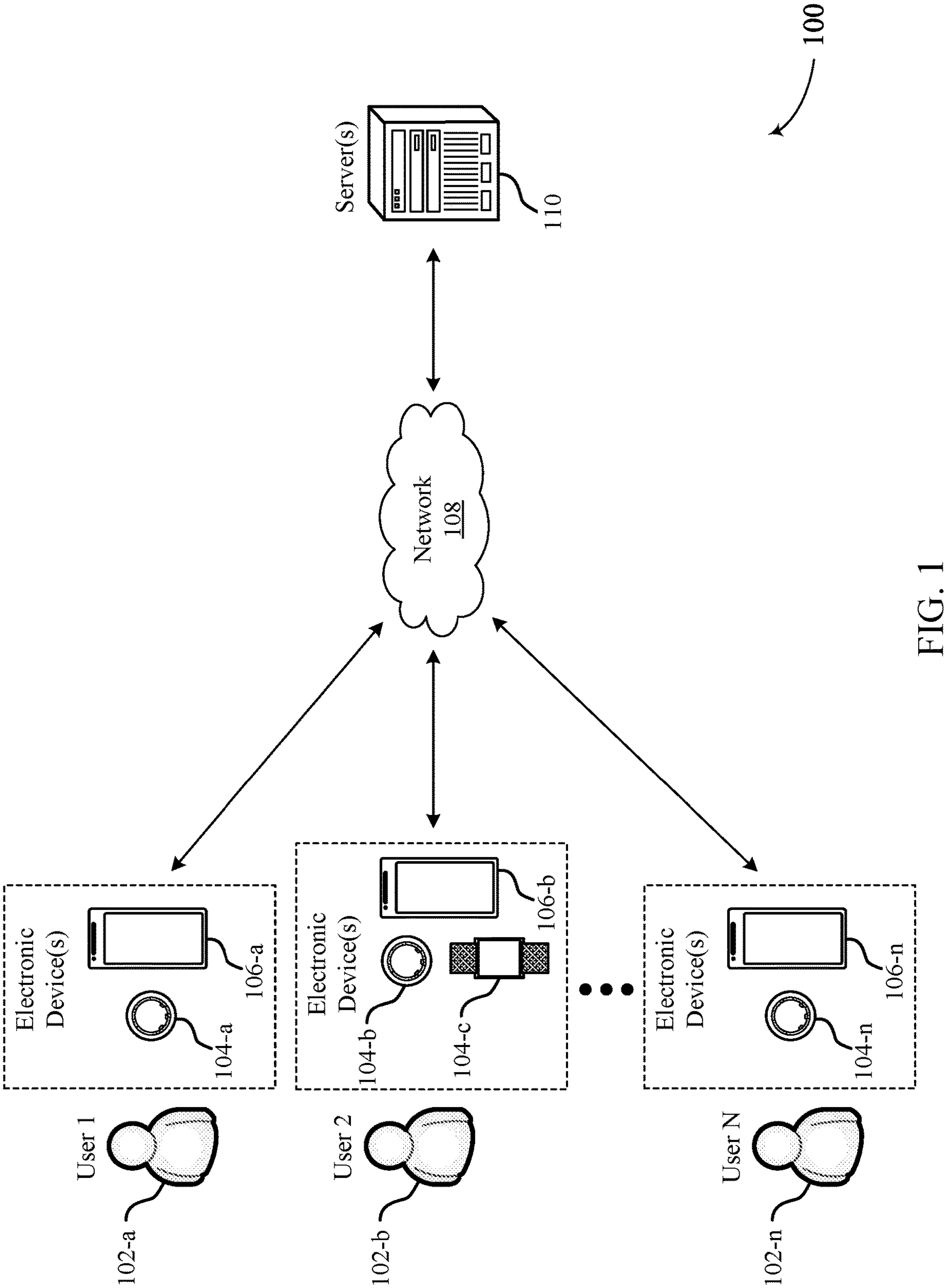
FIG. 1 illustrates an example of a system that supports measuring impact of environmental factors on physiological data collected from a wearable in accordance with aspects of the present disclosure.

A user may use a device, for example, a wearable ring device, to collect, monitor, and track physiological data of the user based on sensor measurements of the wearable ring device. Examples of physiological data may include temperature data, heart rate data, photoplethysmography (PPG) data, and the like. The physiological data collected, monitored, and tracked via the wearable ring device may be used to gain health insights about the user, such as the user's sleeping patterns, activity patterns, and the like. However, a user may desire the ability to gain health insights about the user associated with the impacts of an environment (e.g., weather) on the user, such as on the user's emotional well-being. For example, a user may wear a wearable ring device and the wearable ring device may collect physiological data associated with the user to gain health insights about the user. In some cases, the environment of a user may impact a physiological condition of the user, such as a psychological state or a physical state, and a system associated with the ring wearable device may be unaware that one or more characteristics of the environment impacted the user and, as such, conventional techniques for gaining health insights about a user may be deficient.

Aspects of the present disclosure support techniques for detecting impacts of an environment, specifically weather, on a physical state or a psychological state of a user, specifically on the emotional well-being of the user. In other words, aspects of the present disclosure support a method of receiving environmental data associated with one or more characteristics of an environment in which a user is located, as well as feedback data from a user indicating a physical state or a psychological state of the user when experiencing the one or more characteristics, and determine a set of relationships between the environmental data and the received feedback data, the received physiological data associated with the user, or both. In particular, aspects of the present disclosure are directed to determining a set of recurring relationships associated with environmental data and providing the user with enhanced health insights and recommendations based on the recurring relationships.

In some cases, a system may collect physiological data associated with a user, such as monitoring the sleep of the user, the heart rate of the user, the temperature of the user, or the like, via one or more sensors of a wearable ring device. In some cases, the user may provide feedback data associated with a psychological state or a physical state of the user to a system associated with the wearable ring device. For example, a graphical user interface (GUI) on a mobile device associated with the wearable ring device may prompt the user to select one or more tags associated with the psychological state of the user or the physical state of the user, such as prompting the user to report if they are happy or sad, or if they are experiencing a headache or a sore throat. Additionally, the system may receive environment data including one or more characteristics of an environment in which the user is located, such as the temperature, air quality, air pressure, or the like.

Continuing with the same example, the system may determine one or more relationships between the environmental data and the feedback data, the physiological data, or both. For example, the system may determine that on a day with poor air quality, the user reported experiencing a headache, and that the headache may be a result of the poor air quality. Additionally, the system may identify a reoccurrence of a relationship and provide recommendations to the user when the user is exposed to an environmental characteristic associated with the recurring relationship or is predicted to be exposed to environmental characteristic associated with the recurring relationship. In particular, the system may provide a recommendation to the user to preempt a physiological response (e.g., physical response or psychological response) of the user, remediate the physiological response of the user, or both, based on the recurring relationship. Continuing with the previous example, the system may identify that a quantity of reporting instances are associated with the user reporting experiencing a headache on days with poor air quality (e.g., air quality below a threshold quality), where the quantity of reporting instances exceeds a threshold quantity. As such, the system may determine a relationship between the poor air quality and the user experiencing a headache.

Additionally, the system may identify (e.g., via a weather application) that an upcoming day is predicted to have poor air quality and may recommend one or more actions to the user to avoid experiencing a headache, such as taking a pain killer or avoiding time outside. Similarly, the system may prompt the user to provide feedback when experiencing an environmental characteristic based on the recurring relationship. For example, the system may identify an environmental characteristic associated with a recurring relationship and may prompt the user to report whether they are experiencing a physical state or a psychological state that they have previously reported when exposed to the environmental characteristic based on the recurring relationship.

The system may also determine one or more trends associated with one or more relationships. For example, the system may identify that in summer months, the user tends to have a Sleep Score above a certain value and in winter months, the user tends to have a Sleep Score below the certain value. In some cases, the system may utilize the trends to provide health insights to the user, such as providing guidance as to why the user may be reporting a certain psychological state, a certain physical state, or may be experiencing a certain physiological response.

While much of the present disclosure is described in the context of weather conditions, this is not to be regarded as a limitation of the present disclosure. Indeed, it is contemplated herein that environmental data may include any characteristic of an environment, including a weather condition. In this regard, other environmental characteristics associated with an environment of the user may include a noise level of an environment, one or more characteristics associated with an indoor environment, an ambient light value, or the like.

Aspects of the disclosure are initially described in the context of systems supporting physiological data collection from users via wearable devices. Aspects of the disclosure are then described in the context of a GUI. Aspects of the disclosure are further illustrated by and described with reference to apparatus diagrams, system diagrams, and flowcharts that relate to measuring impact of environmental factors on physiological data collected from a wearable.

FIG. 1 illustrates an example of a system 100 that supports measuring impact of environmental factors on physiological data collected from a wearable in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) that emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof. In general, the terms light-emitting components, light-emitting elements, and like terms, may include, but are not limited to, LEDs, micro LEDs, mini LEDs, laser diodes (LDs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time during which a user 102 is asleep, and classify periods of time during which the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time during which the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for detecting impacts of environmental factors on a physical state or a psychological state of a user 102, specifically on the emotional well-being of the user 102. In particular, the system 100 illustrated in FIG. 1 may support techniques for receiving physiological data associated with the user 102 via a ring 104, environmental data including one or more characteristics of an environment associated with the user 102, and feedback data indicating a physical or a psychological state of the user 102 when experiencing the one or more characteristics of the environment. Additionally, the system 100 may support determining a set of relationships between the environmental data and the physiological data, the feedback data, or both, and generating a message for the user 102 based on the set of relationships. For example, as shown in FIG. 1, a user 102-*a* may be associated with a ring 104-*a* and a user device 106-*a*. In this example, the ring 104-*a* may collect physiological data associated with the user. Additionally, the system 100 may receive environmental data including one or more characteristics of an environment associated with the user 102-*a*, for example, via an application on the user device 106-*a*. Further, the system 100 may prompt the user 102-*a* to provide feedback data via an application associated with the ring 104-*a* on the user device 106-*a*.

The system 100 may determine a set of relationships between the received environmental data and the received feedback data, the received physiological data, or both. Additionally, the system 100 may generate a message for the user 102-*a* including a set of instructions for regulating the physical state of the user 102-*a*, the psychological state of the user 102-*a*, or both, when experiencing the environmental characteristic based on the set of relationships and may display the message to the user 102-*a* via a GUI on the user device 106-*a*. In some implementations, the system 100 may determine a recurrence of a relationship and may display a message to the user 102-*a* based on the recurrence. In some cases, the message may include a suggested action for the user 102-*a* based on identifying a predicted or estimated environmental characteristic associated with the recurring relationship.

The suggested action may preempt a physiological response of the user 102-*a* or remediate the physiological response of the user 102-*a*, where the physiological response corresponds to the physical state of the user 102-*a*, the psychological state of the user 102-*a*, or both. For example, the system 100 may identify a relationship between the user 102-*a* reporting experiencing a headache and the air quality. Additionally, the system 100 may identify that this relationship has occurred a quantity of times that exceeds a threshold quantity. As such, the system 100 may determine that when the air quality is poor, the user 102-*a* is likely to experience a headache and may prompt the user 102-*a* to avoid the outdoors or take a pain killer when the environment is predicted or estimated to be associated with a poor air quality. In some implementations, the system 100 may determine a trend over a duration based on the set of relationships and may display an indication of the trend to the user 102-*a* via the GUI. For example, the system 100 may identify that from September to November the user 102-*a* tends to report, based on feedback data, experiencing congestion and tends to experience, based on physiological data, an elevated temperature. Thus, the system 100 may determine that the user tends to experience allergies in the fall months.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
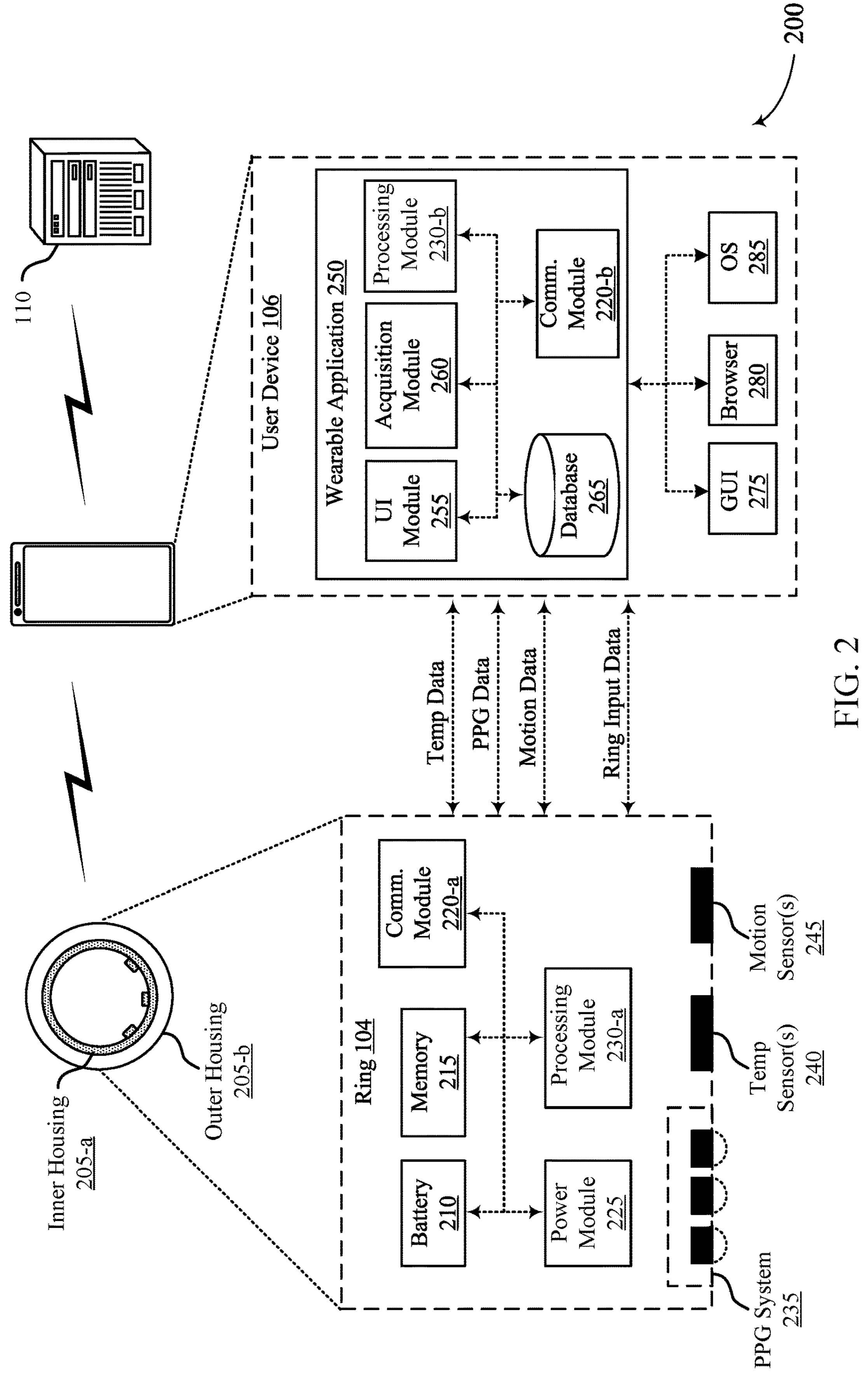
FIG. 2 illustrates an example of a system that supports measuring impact of environmental factors on physiological data collected from a wearable in accordance with aspects of the present disclosure.

FIG. 2 illustrates an example of a system 200 that supports measuring impact of environmental factors on physiological data collected from a wearable in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*a*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240.

The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, that may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 in which the optical receiver(s) receive transmitted light that is reflected through the region of the user's finger. In some implementations, the PPG system 235 may be configured as a transmissive PPG system 235 in which the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS) 285, a web browser application (e.g., web browser 280), one or more additional applications, and a GUI 275. The user device 106 may further include other modules and components, including sensors, audio devices, haptic feedback devices, and the like.

The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time in which the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the ring 104, the mobile device 106, and the servers 110 of the system 200 may support techniques for detecting impacts of environmental factors on a physical state or a psychological state of a user, specifically on the emotional well-being of the user. In particular, the system 200 illustrated in FIG. 2 may support techniques for receiving physiological data associated with the user via one or more sensors on the ring 104 (e.g., the PPG system 235, the temperature sensors 240, the motion sensors 245, or any combination thereof), environmental data including one or more characteristics of an environment associated with the user via one or more applications on the user device 106, and feedback data indicating a physical or a psychological state of the user when experiencing the one or more characteristics of the environment via a GUI 275 on the user device 106. For example, the system 200 may prompt the user to select one or more contextual tags associated with a psychological state of the user or a physical state of the user via the GUI 275. Additionally, the system 200 may determine, via a processing module 230, a set of relationships between the environmental data and the physiological data, the feedback data, or both, and generate a message for the user based on the set of relationships to be displayed via the GUI 275. For example, upon receiving the environmental data, the system may analyze feedback data or physiological data received while the user was experiencing an environmental characteristic associated with the environmental data to determine whether the environmental characteristic may cause or impact the feedback data of physiological data received.

In some cases, the system 200 may store the set of relationships in a database 265 and may determine a recurrence of a relationship from the set of relationships. For example, the system may store occurrences of a relationship in the database 265 and may identify that the relationship is recurring based on a quantity of occurrences of the relationship exceeding a threshold. In some case, the system 200 may display an indication of the recurrency to the user 102 via the GUI 275. In some implementations, the system 200 may determine a trend over a duration based on the set of relationships stored in the database 265. For example, the system 200 may store each occurrence of a relationship of the set of relationships with an associated time stamp (e.g., time, date, day of a week, month, year, or any combination thereof). Additionally, the system 200 may identify a trend between when occurrences of the relationship occur based on the time stamp data and the relationship itself.

Figure 3:
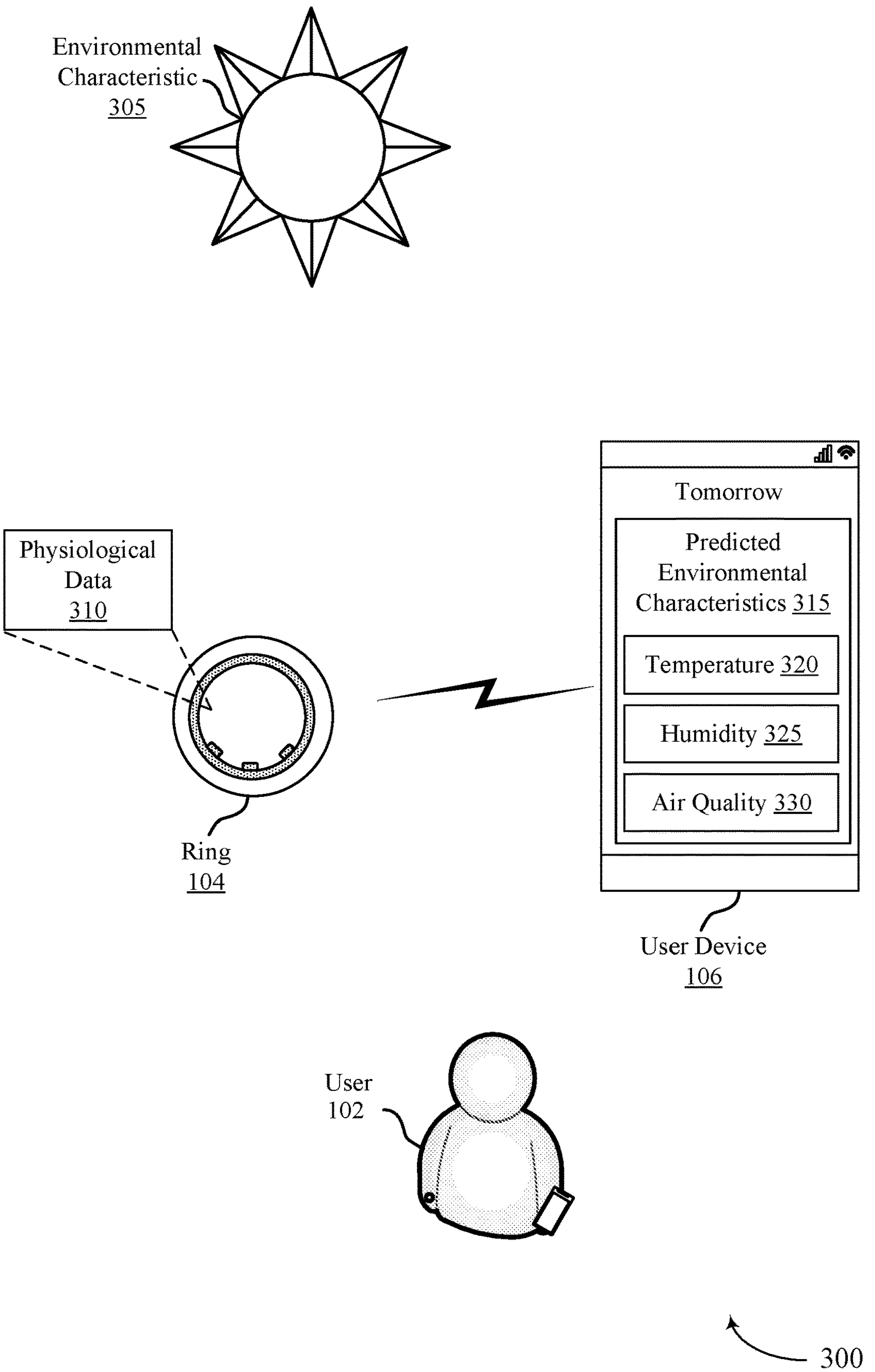
FIG. 3 illustrates an example of a system that supports measuring impact of environmental factors on physiological data collected from a wearable in accordance with aspects of the present disclosure.

FIG. 3 illustrates an example of a system 300 that supports measuring impact of environmental factors on physiological data collected from a wearable in accordance with aspects of the present disclosure. The system 300 may implement, or be implemented by, aspects of the system 100, the system 200, or both. For example, the user 102 may wear a ring 104 and be associated with a user device 106 (e.g., a smartphone), as described with respect to the system 100 and the system 200.

In some cases, the user 102 may be exposed to an environmental characteristic 305 and the system 300 may receive environmental data associated with the environmental characteristic 305 (e.g., within a threshold duration). In some cases, the system 300 may receive the environmental data via one or more applications on the user device 106. For example, the system 300 may receive environmental data, such as an air pressure value, a humidity value, a temperature value, an air quality value, or any combination thereof, from a weather application on the user device 106. Additionally, or alternatively, the system 300 may receive environmental data via one or more sensors on the ring 104, the user device 106, or both. For example, the system 300 may receive environmental data, such as a noise value or an ambient light value, via one or more sensors on the user device 106.

Additionally, the ring 104 may collect physiological data 310 associated with the user 102 while experiencing the environmental characteristic 305 and an application on the user device 106 (e.g., a wearable application 250 as described with respect to FIG. 2) may receive feedback data from the user 102 while experiencing the environmental characteristic 305. The feedback data may include classifier data (e.g., one or more contextual tags) associated with a physical state of the user 102, an emotion state of the user 102, or both.

In some cases, the system 300 may determine one or more relationships between the environmental characteristic 305 and the physiological data 310, the feedback data, or both. For example, the system 300 may identify that on a sunny day above 80 degrees the user 102 reporting feeling happy and had a Readiness Score 5 points above the average Readiness Score of the user 102. Additionally, the system 300 may store determined relationships and a quantity of occurrences of the determined relationships in a database, such that the system 300 may determine a recurrency of one or more relationships. In particular, the system 300 may determine that a relationship is recurring based on a the quantity of occurrences exceeding a threshold quantity. In such cases, the system 300 may identify that when the user 102 experiences an environmental characteristic associated with a recurring relationship, the user 102 is likely to experience a physiological response (e.g., a change in psychological state or a change in physical state) also associated with the recurring relationship.

In some embodiments, the system 300 may determine one or more trends associated with one or more relationships. For example, the system 300 may determine that a user 102 experiences certain relationships during summer months (e.g., based on timestamps associated with the certain relationships) and experiences certain other relationships during winter months. For example, the system 300 may identify that the user 102 tends to experience a lower resting heart rate, an increase in sleep quality, and an increase in calories burned from April to August while, in the months from October to February, the user 102 tends to experience a higher resting heart rate, a decrease in sleep quality, and a decrease in calories burned. In such cases, the system 300 may identify that the change in physiological state of the user 102 between the two time periods may be associated with changes in the environment (e.g., changes in weather) and that the user 102 may be experiencing seasonal affected disorder.

In some cases, the system 300 may display a message, via the user device 106, including instructions for regulating the physical state of the user 102, the psychological state of the user 102, or both when experiencing an environmental characteristic 305 associated with a relationship. For example, the system 300 may identify that it is a sunny day above 80 degrees and that when the user 102 takes a 30 minute walk on sunny days above 75 degrees, the user 102 experiences an increase in a Readiness Score associated with the user 102 and reports feeling happy. As such, the system 300 may recommend, via a GUI on the user device 106, that the user 102 go outside and take a walk. In some cases, the recommendation message may also include an indication of the relationship (e.g., to tell the user 102 why they should perform the suggested action). In another example, the system 300 may provide the user 102 with an indication of why they may be experiencing a certain physiological response based on one or more relationships. For example, the system 300 may identify that it is a cloudy day below 40 degrees and that when the user 102 is exposed to cloudy days below 50 degrees, the user 102 reports feeling sad and experiences a decrease in calories burned. As such, the system 300 may display a message to the user 102 asking the user 102 if they are feeling sad and, if so, it is likely due to the weather.

In some cases, the system 300 may display a message to the user 102 including one or more recommendations based on one or more recurring relationships. For example, the system 300 may identify a recurring relationship that when the user 102 is exposed to an ambient light value above a threshold, the user 102 experiences poor sleep. The system 300 may also identify, via an application on the user device 106 (e.g., an application that controls lights in the home of the user 102), that when the user 102 goes to sleep, the ambient light value in the room of the user 102 is typically above the threshold. As such, the system 300 may recommend that the user 102 turn off one or more lights in their home prior to sleeping to reduce the ambient light level (e.g., to below the threshold) to improve the sleep quality of the user 102. Additionally, or alternatively, the system 300 may prompt the user 102 to input feedback data when the system 300 identifies an environmental characteristic 305 associated with a recurring relationship, where the prompt includes one or more tags that the user 102 has previously reported based on the recurring relationship (e.g., the system 300 provides the user 102 with smart guesses as to what the user 102 may be feeling).

In some cases, the system 300 may identify a predicted (e.g., estimated) environmental characteristic 315 that the user 102 is expected to experience within a threshold duration. For example, the system 300 may determine, via an application on the user device 106, that the user 102 is located in an environment that is associated with predicted environmental characteristics 315 (e.g., predicted weather) including a temperature 320, a humidity 325, and an air quality 330. Additionally, the system 300 may identify that one or more relationships (e.g., associated with the user 102) is related to one or more of the predicted environmental characteristics 315. As such, the system 300 may recommend an action to the user 102 to preempt or remediate a physiological response of the user 102 associated with the one or more relationships. For example, the system 300 may identify that the humidity 325 is predicted to be below a threshold value and when that occurs, the user 102 typically reports feeling dehydrated. As such, the system 300 may display a message to the user 102 recommending that the user 102 increase their water intake prior to being exposed to the predicted environmental characteristics 315.

In some cases, the system 300 may predict relationships that the user 102 may experience based on other relationships determined by the system 300. In other words, the system 300 may determine that the user 102 associated with a first relationship is likely to be associated with a second relationship (e.g., based on relationship and/or trend data for a database of users) and may provide recommendations based on the second relationship as well as the first relationship. For example, the system 300 may determine, based on one or more relationships associated with the user 102, that the user 102 experiences certain physiological responses based on changes in air pressure. The system 300 may also identify that physiological responses experienced based on changes in air pressure are often also experienced based on changes in temperature. As such, the system 300 may recommend actions to the user 102 to preempt or resolve the certain physiological responses when the user 102 is exposed, or predicted to be exposed, to changes in air pressure, as well as when the user 102 is exposed, or predicted to be exposed, to changes in temperature.

Figure 4:
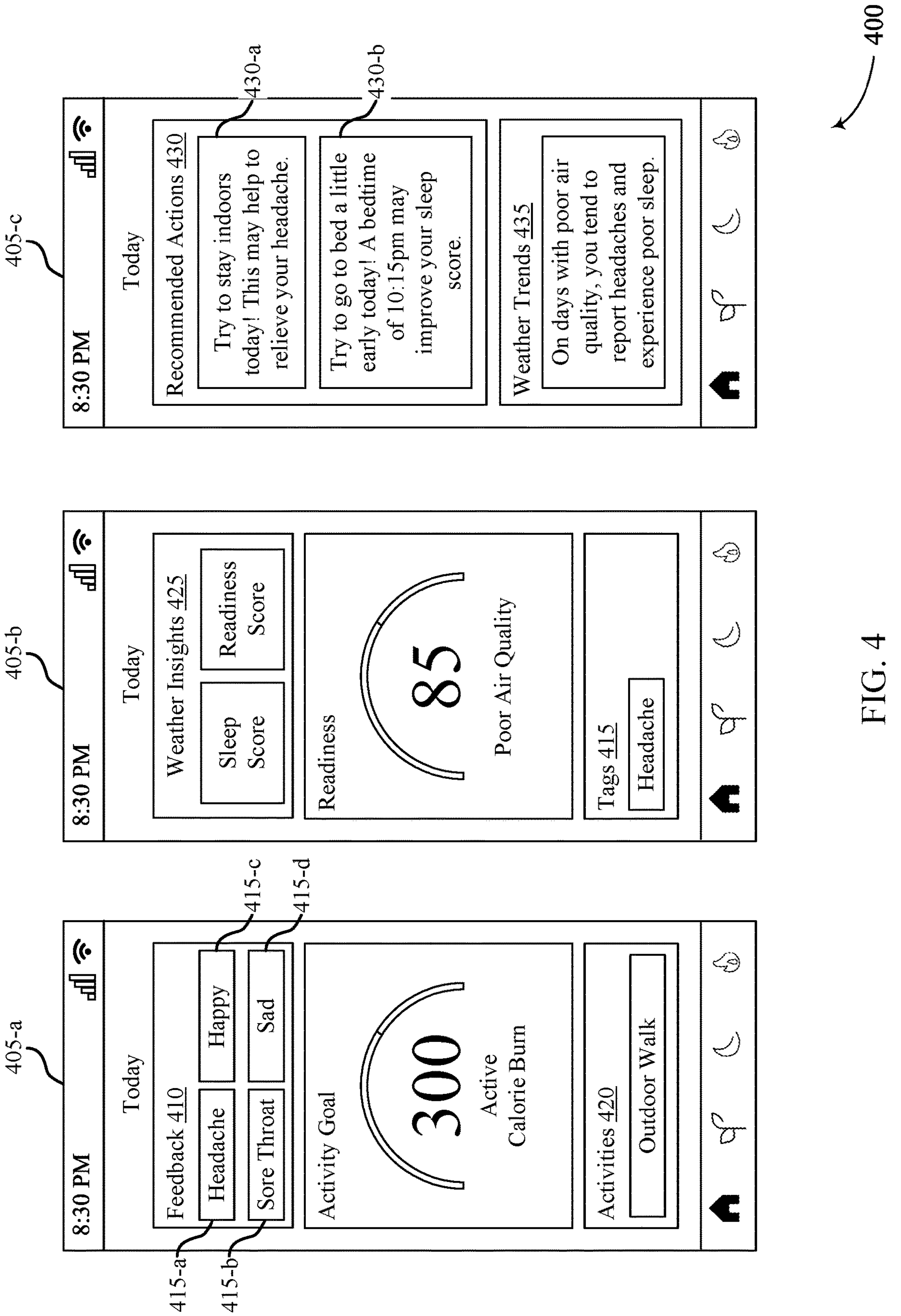
FIG. 4 illustrates an example of a graphical user interface (GUI) that supports measuring impact of environmental factors on physiological data collected from a wearable in accordance with aspects of the present disclosure.

FIG. 4 illustrates examples of a GUI 400 that supports measuring impact of environmental factors on physiological data collected from a wearable in accordance with aspects of the present disclosure. The GUI 400 may implement, or be implemented by, aspects of the system 100, the system 200, the system 300, or any combination thereof. For example, the GUI 400 may include an example of the GUI 275 within the user device 106, as described with respect to the system 200.

The GUI 400 illustrates a series of application pages 405 that may be displayed to a user via the GUI 400 (e.g., a GUI 275 illustrated in FIG. 2). Continuing with the example above, the system 200 may receive environmental data including at least one characteristic of an environment associated with the user 102 (e.g., an environment that the user 102 is located in or currently experiencing). In this example, the system 200 may identify, based on data received from an application on the user device 106, that the user 102 is located in an environment has poor air quality. In some cases, the system 200 may prompt the user 102 to input feedback, such as classifier data, indicating a physical state or a psychological state of the user 102 when experiencing the environmental characteristic. As shown in FIG. 4, the application page 405-*a* may prompt the user 102 to provide feedback 410 by selecting one or more tags 415 (e.g., contextual tags). For example, the user 102 may select one or more tags 415 associated with a physical state of the user 102, such as a tag 415-*a* indicating the user 102 is experiencing a headache or a tag 415-*b* indicating the user 102 is experiencing a sore throat. Additionally, the user 102 may select one or more tags 415 associated with a psychological state of the user 102, such as a tag 415-*c* indicating the user 102 is feeling happy or a tag 415-*d* indicating the user 102 is feeling sad. The system 200 may also allow the user 102 to input feedback pertaining to activities in which the user 102 has participated, such as activities 420, that may be associated with physiological data collected by a ring 104 worn by the user 102.

In some cases, the system 200 may determine a set of relationships between received environmental data and received physiological data, received feedback data, or both. For example, the system 200 may determine that the tag 415-*a* indicating a headache and the elevated heart rate may be at least partially due to the poor air quality experienced by the user 102. Additionally, the system 200 may generate a message for the user 102 based on the determined relationship. For example, an application page 405-*b* may display weather insights 425 to the user 102 indicating that the user 102 is likely experiencing a headache due to the poor air quality. In some cases, the weather insights 425 may display an indication of how the environmental characteristic, such as the poor air quality, is impacting one or more scores, such as a Sleep Score or a Readiness Score, associated with the user 102. For example, the system 200 may display that the user's 102 Readiness Score is lower than usual due to the poor air quality. The application page 405-*b* may also display an indication of the tags 415 that the user 102 has reported.

Upon selecting the weather insights 425, the user 102 may access an application page 405-*c*. The application page 405-*c* may display recommend actions 430 based on the determined relationship to preempt or resolve a physiological response of the user 102, such as a psychological response or a physical response. For example, the application page 405-*c* may display a message to the user 102 indicating a recommended action 430-*a* (e.g., a suggested action) recommending that the user 102 stay indoors to avoid exposure to the poor air quality and to alleviate the headache experienced by the user 102. Additionally, or alternatively, the message to the user 102 may indicate a suggested content based on a respective effectiveness of the at least one characteristic of the environment on the physical state of the user 102, the psychological state of the user 102, or both. The suggested content may include audio content, video content, textual content, or any combination thereof. For example, the suggested content may help the user 102 understand the effects, or overall help the user 102 understand an association between environmental factors and the user 102 body and/or mind.

In some cases, the set of relationships may be recorded/logged in a database. For example, the system 200 may log the relationship that when the user 102 was in an environment with poor air quality, the user reported the tag 415-*a* associated with a headache and also experienced an elevated heart rate. Additionally, the system 200 may record the quantity of instances in which the user 102 experiences a relationship, such that the system 200 may identify a recurrency of the relationship. In some cases, the system 200 may identify that the quantity of instances in which a user 102 experiences the relationship exceeds a threshold and may determine that the relationship is associated with a trend. Additionally, the system 200 may analyze one or more trends to determine one or more relationships between trends. For example, the system 200 may identify a trend that on days with poor air quality, the user tends to report headaches and experience an elevated heart rate. The system 200 may also identify a trend that on days with poor air quality, the user 102 may also experience poor sleep and the system 200 may determine that the headaches and elevated heart rate experienced due to the poor air quality may result in the poor sleep. In some cases, the system 200 may display weather trends 435 to the user 102 via the application page 405-*c*. For example, the system 200 may display the weather trend 435 indicating that on days with poor air quality, the user tends to report headaches and experience poor sleep.

Additionally, the system 200 may display a recommended action 430 (e.g., a suggested action) based on the weather trends 435. For example, the system 200 may display a recommended action 430-*b* to the user 102, recommending that the user 102 go to be at a certain time such that the user 102 may preempt experiencing poor sleep due to the headaches experienced based on the poor air quality.

In some cases, the recommended actions 430 may include recommended actions based on estimated environmental characteristics. For example, the system 200 may identify that the user is predicted to be exposed to an environment (e.g., within a threshold duration) associated with a stored relationship or trend and may recommend one or more actions for the user 102 to perform such that the user 102 may preempt a physiological response associated with the trend. For example, the system 200 may identify that the user 102 has plans to travel to a certain environment (e.g., identified via one or more applications executable on the user device 106) and may identify that the environment the user 102 is traveling to is associated with high temperatures. The system 200 may also identify that when exposed to high temperatures, the user tends to report feeling dizzy and tends to experience an elevated heart rate. As such, the system 200 may recommend that the user 102 increase their water intake 3 days prior to traveling to the environment to mitigate (e.g., avoid) feeling dizzy and/or experiencing the elevated heart rate.

Figure 5:
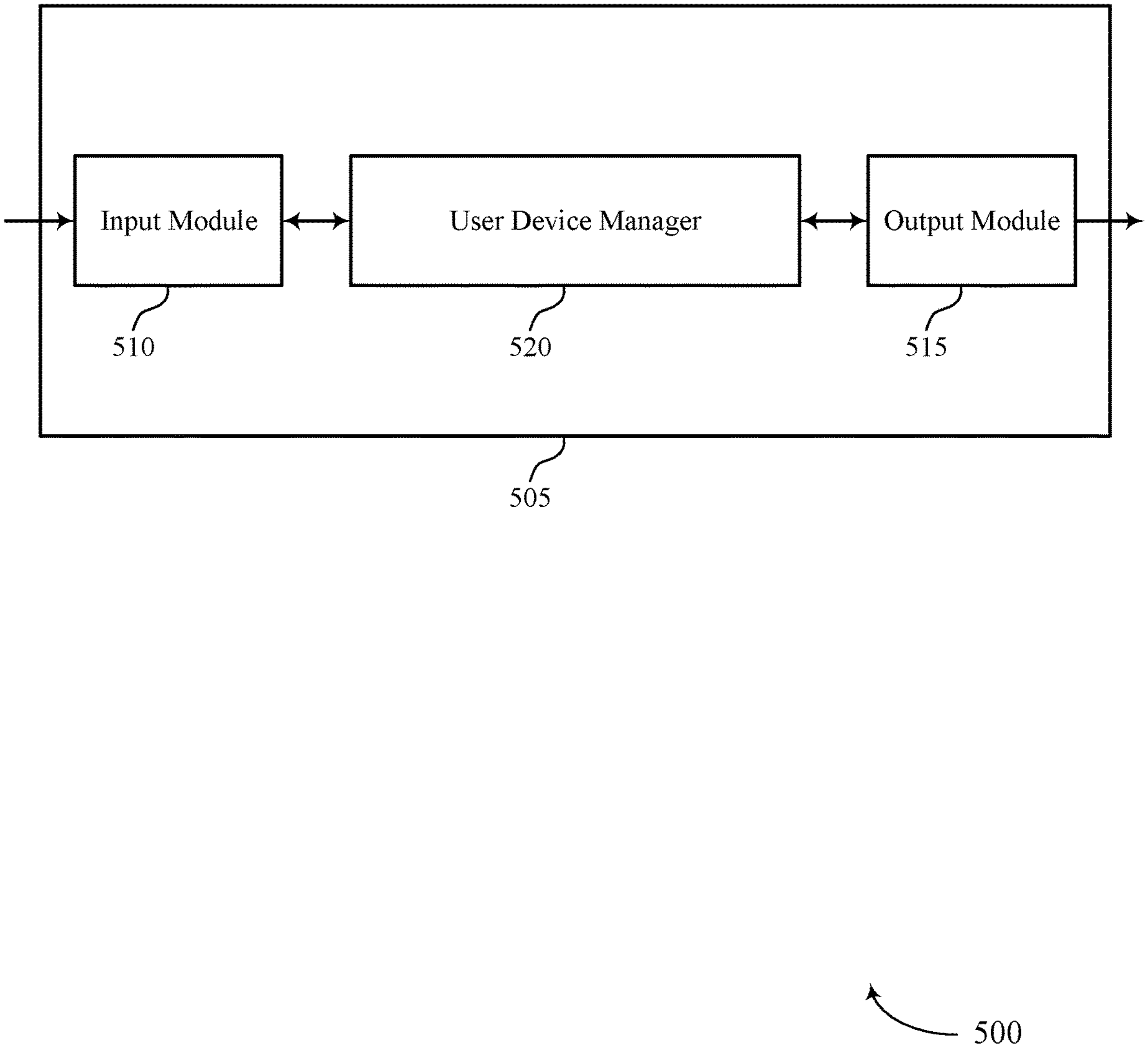
FIGS. 5 and 6 show block diagrams of devices that support measuring impact of environmental factors on physiological data collected from a wearable in accordance with aspects of the present disclosure.

FIG. 5 shows a block diagram 500 of a device 505 that supports measuring impact of environmental factors on physiological data collected from a wearable in accordance with aspects of the present disclosure. The device 505 may be an example of aspects of a user device as described herein. The device 505 may include an input module 510, an output module 515, and a user device manager 520. The device 505 may also include a processor. Each of these components may be in communication with one another (e.g., via one or more buses).

The user device manager 520, the input module 510, the output module 515, or various combinations thereof or various components thereof may be examples of means for performing various aspects of measuring impact of environmental factors on physiological data collected from a wearable as described herein. For example, the user device manager 520, the input module 510, the output module 515, or various combinations or components thereof may support a method for performing one or more of the functions described herein.

In some examples, the user device manager 520, the input module 510, the output module 515, or various combinations or components thereof may be implemented in hardware (e.g., in communications management circuitry). The hardware may include a processor, a DSP, an ASIC, an FPGA or other programmable logic device, a discrete gate or transistor logic, discrete hardware components, or any combination thereof configured as or otherwise supporting a means for performing the functions described in the present disclosure. In some examples, a processor and memory coupled with the processor may be configured to perform one or more of the functions described herein (e.g., by executing, by the processor, instructions stored in the memory).

Additionally, or alternatively, in some examples, the user device manager 520, the input module 510, the output module 515, or various combinations or components thereof may be implemented in code (e.g., as communications management software or firmware) executed by a processor. If implemented in code executed by a processor, the functions of the user device manager 520, the input module 510, the output module 515, or various combinations or components thereof may be performed by a general-purpose processor, a DSP, a CPU, an ASIC, an FPGA, or any combination of these or other programmable logic devices (e.g., configured as or otherwise supporting a means for performing the functions described in the present disclosure).

For example, the user device manager 520 may be configured as or otherwise support a means for receiving physiological data associated with a user from a wearable device. The user device manager 520 may be configured as or otherwise support a means for receiving environmental data comprising at least one characteristic of an environment of the user. The user device manager 520 may be configured as or otherwise support a means for receiving feedback data from the user indicating a physical state or a psychological state of the user when experiencing the at least one characteristic of the environment. The user device manager 520 may be configured as or otherwise support a means for determining a set of relationships between the received environmental data and the received feedback data, the received physiological data, or both. The user device manager 520 may be configured as or otherwise support a means for generating a message for the user based at least in part on the set of relationships, wherein the message comprises instructions for regulating the physical state of the user, the psychological state of the user, or both, when experiencing the at least one characteristic of the environment. The user device manager 520 may be configured as or otherwise support a means for causing a GUI of a user device to display the message for the user.

By including or configuring the user device manager 520 in accordance with examples as described herein, the device 505 (e.g., a processor controlling or otherwise coupled with the input module 510, the output module 515, the user device manager 520, or a combination thereof) may support techniques for measuring impact of environmental factors on physiological data collected from a wearable that may result in enhanced health insights and recommendations to preempt or resolve physiological responses associated with the weather impacts, specifically negative physiological responses.

Figure 6:
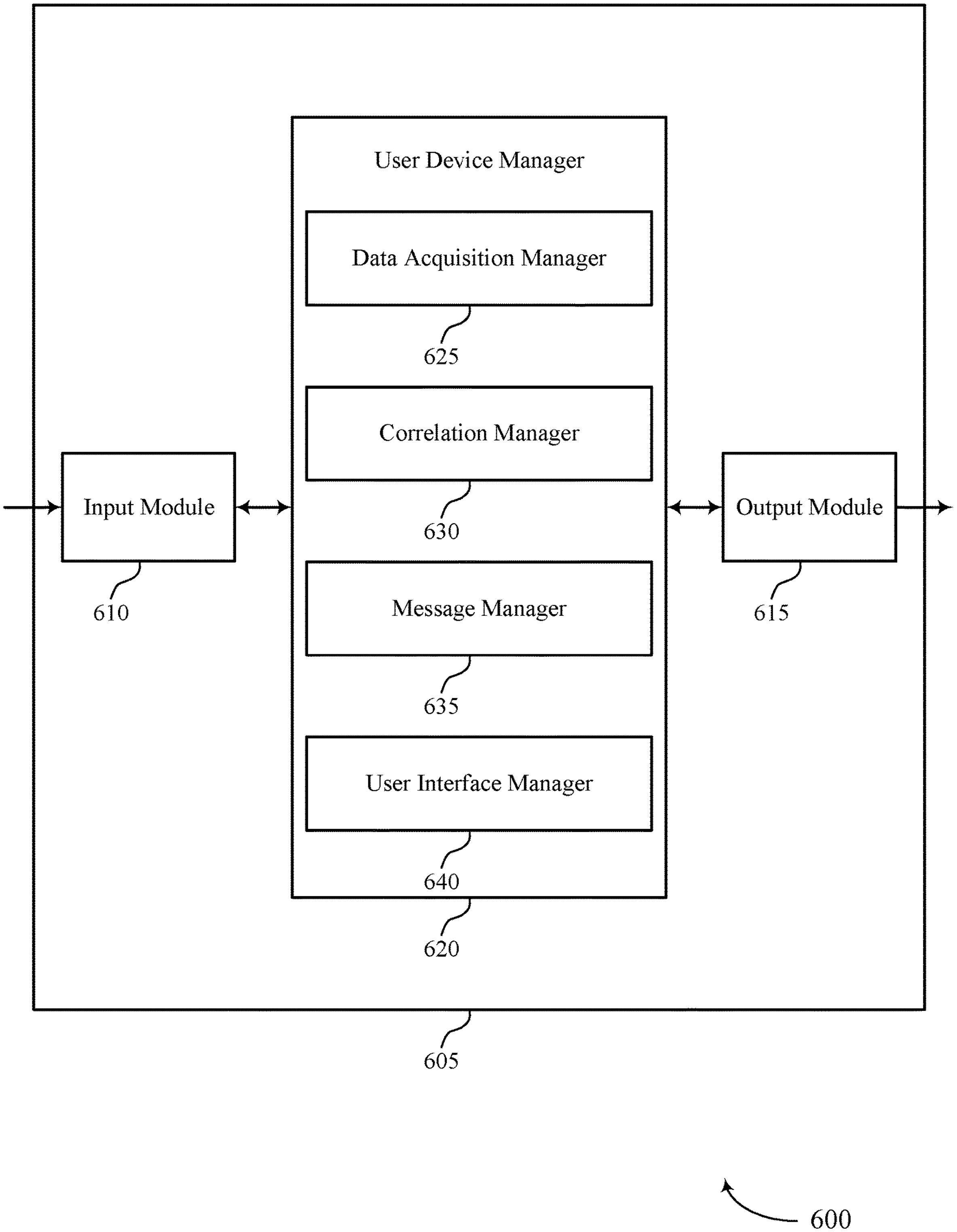

FIG. 6 shows a block diagram 600 of a device 605 that supports measuring impact of environmental factors on physiological data collected from a wearable in accordance with aspects of the present disclosure. The device 605 may be an example of aspects of a device 505 or a user device 106 as described herein. The device 605 may include an input module 610, an output module 615, and a user device manager 620. The device 605 may also include a processor. Each of these components may be in communication with one another (e.g., via one or more buses).

The device 605, or various components thereof, may be an example of means for performing various aspects of measuring impact of environmental factors on physiological data collected from a wearable as described herein. For example, the user device manager 620 may include a data acquisition manager 625, a correlation manager 630, a message manager 635, a user interface manager 640, or any combination thereof. The user device manager 620 may be an example of aspects of a user device manager 520 as described herein. In some examples, the user device manager 620, or various components thereof, may be configured to perform various operations (e.g., receiving, monitoring, transmitting) using or otherwise in cooperation with the input module 610, the output module 615, or both. For example, the user device manager 620 may receive information from the input module 610, send information to the output module 615, or be integrated in combination with the input module 610, the output module 615, or both to receive information, transmit information, or perform various other operations as described herein.

The data acquisition manager 625 may be configured as or otherwise support a means for receiving physiological data associated with a user from a wearable device. The data acquisition manager 625 may be configured as or otherwise support a means for receiving environmental data comprising at least one characteristic of an environment of the user. The data acquisition manager 625 may be configured as or otherwise support a means for receiving feedback data from the user indicating a physical state or a psychological state of the user when experiencing the at least one characteristic of the environment. The correlation manager 630 may be configured as or otherwise support a means for determining a set of relationships between the received environmental data and the received feedback data, the received physiological data, or both. The message manager 635 may be configured as or otherwise support a means for generating a message for the user based at least in part on the set of relationships, wherein the message comprises instructions for regulating the physical state of the user, the psychological state of the user, or both, when experiencing the at least one characteristic of the environment. The user interface manager 640 may be configured as or otherwise support a means for causing a GUI of a user device to display the message for the user.

Figure 7:
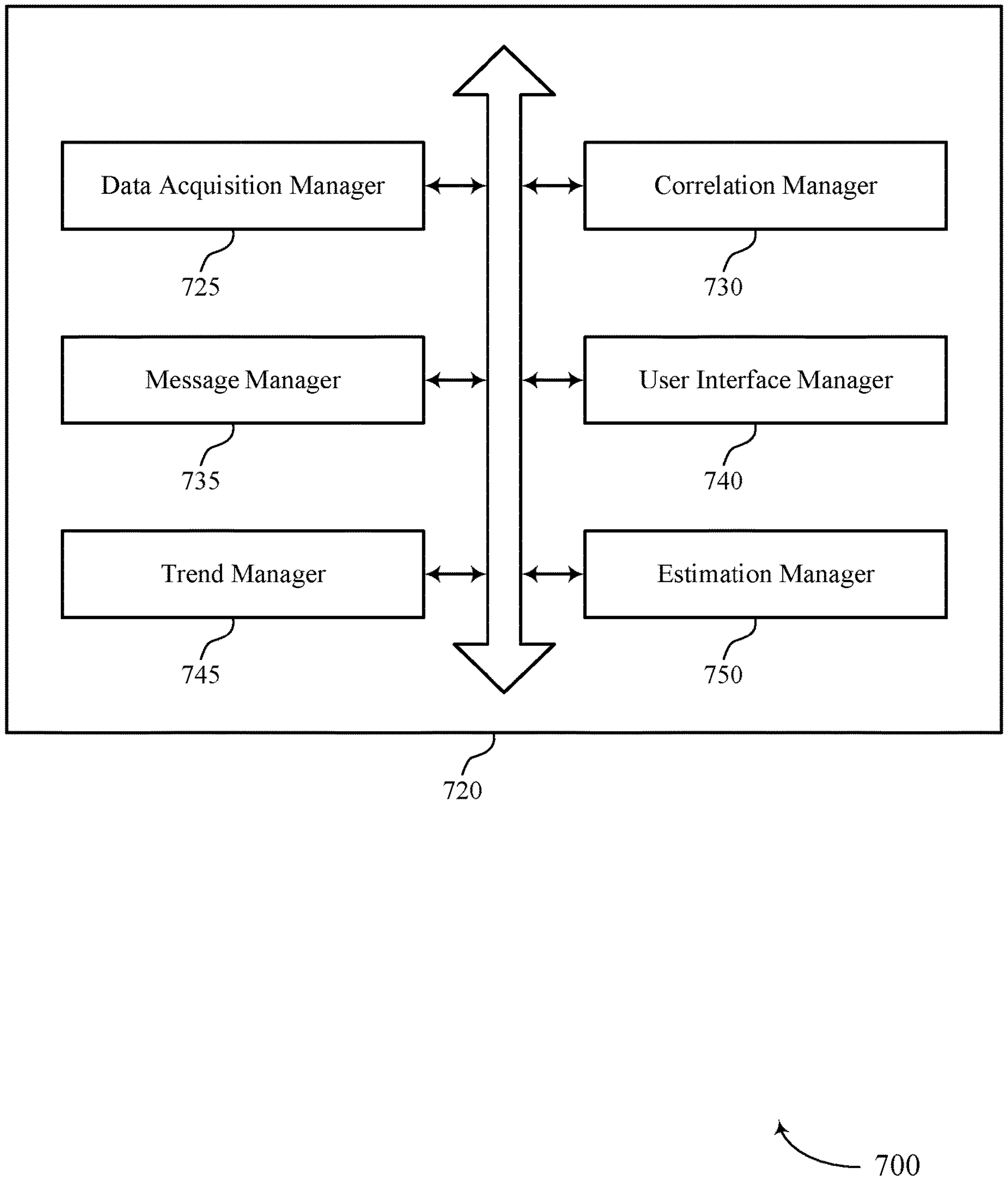
FIG. 7 shows a block diagram of a user device manager that supports measuring impact of environmental factors on physiological data collected from a wearable in accordance with aspects of the present disclosure.

FIG. 7 shows a block diagram 700 of a user device manager 720 that supports measuring impact of environmental factors on physiological data collected from a wearable in accordance with aspects of the present disclosure. The user device manager 720 may be an example of aspects of a user device manager 520, a user device manager 620, or both, as described herein. The user device manager 720, or various components thereof, may be an example of means for performing various aspects of measuring impact of environmental factors on physiological data collected from a wearable as described herein. For example, the user device manager 720 may include a data acquisition manager 725, a correlation manager 730, a message manager 735, a user interface manager 740, a trend manager 745, an estimation manager 750, or any combination thereof. Each of these components may communicate, directly or indirectly, with one another (e.g., via one or more buses).

The data acquisition manager 725 may be configured as or otherwise support a means for receiving physiological data associated with a user from a wearable device. In some examples, the data acquisition manager 725 may be configured as or otherwise support a means for receiving environmental data comprising at least one characteristic of an environment of the user. In some examples, the data acquisition manager 725 may be configured as or otherwise support a means for receiving feedback data from the user indicating a physical state or a psychological state of the user when experiencing the at least one characteristic of the environment. The correlation manager 730 may be configured as or otherwise support a means for determining a set of relationships between the received environmental data and the received feedback data, the received physiological data, or both. The message manager 735 may be configured as or otherwise support a means for generating a message for the user based at least in part on the set of relationships, wherein the message comprises instructions for regulating the physical state of the user, the psychological state of the user, or both, when experiencing the at least one characteristic of the environment. The user interface manager 740 may be configured as or otherwise support a means for causing a GUI of a user device to display the message for the user.

In some examples, the data acquisition manager 725 may be configured as or otherwise support a means for detecting the at least one characteristic of the environment within a threshold duration. In some examples, the message manager 735 may be configured as or otherwise support a means for generating, in response to detecting the at least one characteristic of the environment within the threshold duration, the message for the user.

In some examples, the trend manager 745 may be configured as or otherwise support a means for determining a trend over a duration based at least in part on of the set of relationships between the received environmental data and the received feedback data, the received physiological data, or both. In some examples, the user interface manager 740 may be configured as or otherwise support a means for wherein causing the GUI of the user device to display the message for the user is based at least in part on the determined trend over the duration.

In some examples, the trend manager 745 may be configured as or otherwise support a means for determining a recurrency of at least one relationship of the set of relationships between the received environmental data and the received feedback data, the received physiological data, or both. In some examples, the user interface manager 740 may be configured as or otherwise support a means for wherein causing the GUI of the user device to display the message for the user is based at least in part on the recurrency of the at least one relationship of the set of relationships.

In some examples, the trend manager 745 may be configured as or otherwise support a means for determining that the recurrency of the at least one relationship of the set of relationships between the received environmental data and the received feedback data, the received physiological data, or both, satisfies a threshold. In some examples, the user interface manager 740 may be configured as or otherwise support a means for wherein causing the GUI of the user device to display the message for the user is based at least in part on the recurrency of the at least one relationship satisfying the threshold.

In some examples, the estimation manager 750 may be configured as or otherwise support a means for identifying at least one estimated characteristic of the environment based at least in part on the received environmental data. In some examples, the user interface manager 740 may be configured as or otherwise support a means for wherein causing the GUI of the user device to display the message for the user is based at least in part on the at least one estimated characteristic of the environment.

In some examples, the estimation manager 750 may be configured as or otherwise support a means for determining a suggested action to preempt a physiological response of the user or remediate the physiological response of the user, or both, based at least in part on the at least one estimated characteristic of the environment, the physiological response corresponding to the physical state of the user, the psychological state of the user, or both, wherein the message comprises the suggested action.

In some examples, the estimation manager 750 may be configured as or otherwise support a means for determining a suggested content based at least in part on a respective effectiveness of the at least one characteristic of the environment on the physical state of the user, the psychological state of the user, or both. In some examples, the message includes the suggested content. In some examples, the suggested content includes audio content, video content, textual content, or any combination thereof.

In some examples, the at least one characteristic of the environment comprise a temperature value, a noise value, an ambient light value, an air pressure value, a humidity value, an air quality value, or any combination thereof.

In some examples, the feedback data comprises classifier data indicating the psychological state of the user.

In some examples, the classifier data comprises a contextual tag.

In some examples, to support receiving the environmental data, the data acquisition manager 725 may be configured as or otherwise support a means for receiving the environmental data via one or more applications executable on the user device, the one or more applications comprising a lifestyle application, a social media application, a utility application, an information outlet application, or any combination thereof.

In some examples, the wearable device comprises a wearable ring device.

Figure 8:
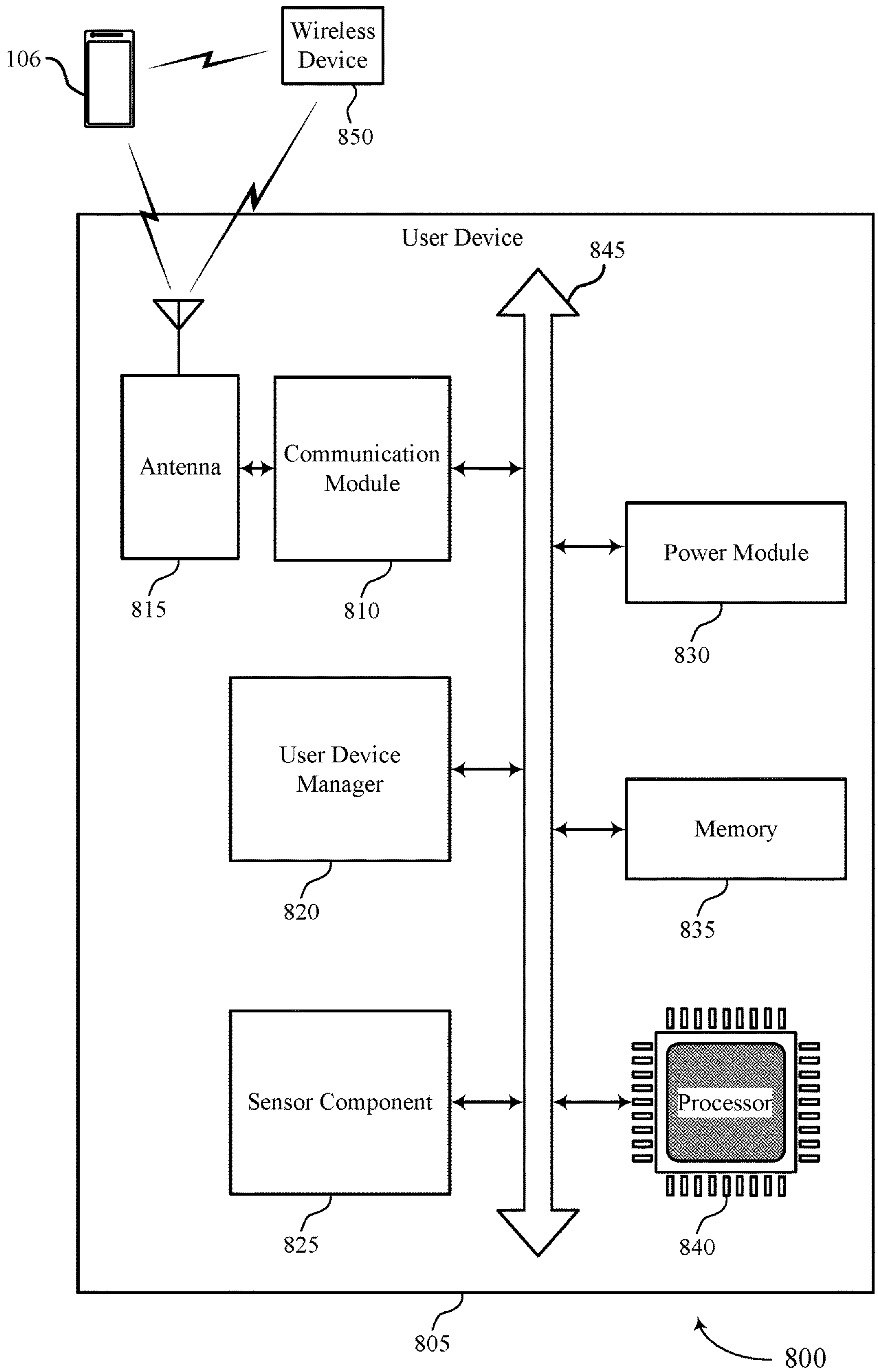
FIG. 8 shows a diagram of a system including a device that supports measuring impact of environmental factors on physiological data collected from a wearable in accordance with aspects of the present disclosure.

FIG. 8 shows a diagram of a system 800 including a device 805 that supports measuring impact of environmental factors on physiological data collected from a wearable in accordance with aspects of the present disclosure. The device 805 may be an example of or include the components of a device 505, a device 605, or a user device as described herein. The device 805 may include an example of a user device 106, as described previously herein. The device 805 may include components for bi-directional communications including components for transmitting and receiving communications with a wearable device 104 and a server 110, such as a user device manager 820, a communication module 810, an antenna 815, a sensor component 825, a power module 830, a memory 835, a processor 840, and a wireless device 850. These components may be in electronic communication or otherwise coupled (e.g., operatively, communicatively, functionally, electronically, electrically) via one or more buses (e.g., a bus 845).

For example, the user device manager 820 may be configured as or otherwise support a means for receiving physiological data associated with a user from a wearable device. The user device manager 820 may be configured as or otherwise support a means for receiving environmental data comprising at least one characteristic of an environment of the user. The user device manager 820 may be configured as or otherwise support a means for receiving feedback data from the user indicating a physical state or a psychological state of the user when experiencing the at least one characteristic of the environment. The user device manager 820 may be configured as or otherwise support a means for determining a set of relationships between the received environmental data and the received feedback data, the received physiological data, or both. The user device manager 820 may be configured as or otherwise support a means for generating a message for the user based at least in part on the set of relationships, wherein the message comprises instructions for regulating the physical state of the user, the psychological state of the user, or both, when experiencing the at least one characteristic of the environment. The user device manager 820 may be configured as or otherwise support a means for causing a GUI of a user device to display the message for the user.

By including or configuring the user device manager 820 in accordance with examples as described herein, the device 805 may support techniques for detecting impacts of weather on the well-being of a user that may result in enhanced health insights and recommendations to preempt or resolve physiological responses associated with the weather impacts, specifically negative physiological responses.

Figure 9:
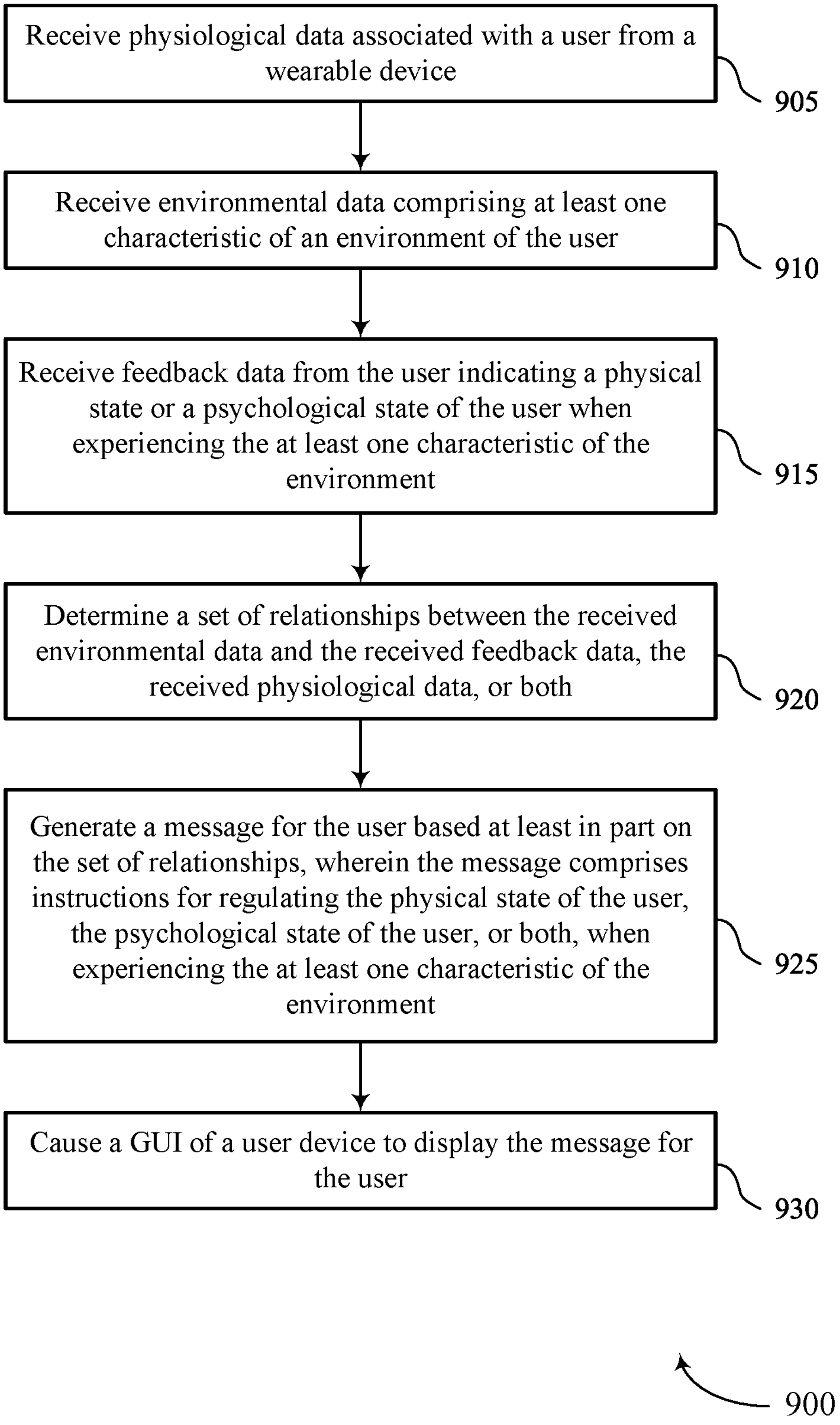
FIG. 9 shows a flowchart illustrating methods that support measuring impact of environmental factors on physiological data collected from a wearable in accordance with aspects of the present disclosure.

FIG. 9 shows a flowchart illustrating a method 900 that supports measuring impact of environmental factors on physiological data collected from a wearable in accordance with aspects of the present disclosure. The operations of the method 900 may be implemented by a user device or its components as described herein. For example, the operations of the method 900 may be performed by a user device as described with reference to FIGS. 1 through 8. In some examples, a user device may execute a set of instructions to control the functional elements of the user device to perform the described functions. Additionally, or alternatively, the user device may perform aspects of the described functions using special-purpose hardware.

At 905, the method may include receiving physiological data associated with a user from a wearable device. The operations of 905 may be performed in accordance with examples as disclosed herein. In some examples, aspects of the operations of 905 may be performed by a data acquisition manager 725 as described with reference to FIG. 7.

At 910, the method may include receiving environmental data comprising at least one characteristic of an environment of the user. The operations of 910 may be performed in accordance with examples as disclosed herein. In some examples, aspects of the operations of 910 may be performed by a data acquisition manager 725 as described with reference to FIG. 7.

At 915, the method may include receiving feedback data from the user indicating a physical state or a psychological state of the user when experiencing the at least one characteristic of the environment. The operations of 915 may be performed in accordance with examples as disclosed herein. In some examples, aspects of the operations of 915 may be performed by a data acquisition manager 725 as described with reference to FIG. 7.

At 920, the method may include determining a set of relationships between the received environmental data and the received feedback data, the received physiological data, or both. The operations of 920 may be performed in accordance with examples as disclosed herein. In some examples, aspects of the operations of 920 may be performed by a correlation manager 730 as described with reference to FIG. 7.

At 925, the method may include generating a message for the user based at least in part on the set of relationships, wherein the message comprises instructions for regulating the physical state of the user, the psychological state of the user, or both, when experiencing the at least one characteristic of the environment. The operations of 925 may be performed in accordance with examples as disclosed herein. In some examples, aspects of the operations of 925 may be performed by a message manager 735 as described with reference to FIG. 7.

At 930, the method may include causing a GUI of a user device to display the message for the user. The operations of 930 may be performed in accordance with examples as disclosed herein. In some examples, aspects of the operations of 930 may be performed by a user interface manager 740 as described with reference to FIG. 7.

It should be noted that the methods described above describe possible implementations, and that the operations and the steps may be rearranged or otherwise modified and that other implementations are possible. Furthermore, aspects from two or more of the methods may be combined.

A method is described. The method may include receiving physiological data associated with a user from a wearable device, receiving environmental data comprising at least one characteristic of an environment of the user, receiving feedback data from the user indicating a physical state or a psychological state of the user when experiencing the at least one characteristic of the environment, determining a set of relationships between the received environmental data and the received feedback data, the received physiological data, or both, generating a message for the user based at least in part on the set of relationships, wherein the message comprises instructions for regulating the physical state of the user, the psychological state of the user, or both, when experiencing the at least one characteristic of the environment, and causing a GUI of a user device to display the message for the user.

An apparatus is described. The apparatus may include a processor, memory coupled with the processor, and instructions stored in the memory. The instructions may be executable by the processor to cause the apparatus to receive physiological data associated with a user from a wearable device, receive environmental data comprising at least one characteristic of an environment of the user, receive feedback data from the user indicating a physical state or a psychological state of the user when experiencing the at least one characteristic of the environment, determine a set of relationships between the received environmental data and the received feedback data, the received physiological data, or both, generate a message for the user based at least in part on the set of relationships, wherein the message comprises instructions for regulating the physical state of the user, the psychological state of the user, or both, when experiencing the at least one characteristic of the environment, and cause a GUI of a user device to display the message for the user.

Another apparatus is described. The apparatus may include means for receiving physiological data associated with a user from a wearable device, means for receiving environmental data comprising at least one characteristic of an environment of the user, means for receiving feedback data from the user indicating a physical state or a psychological state of the user when experiencing the at least one characteristic of the environment, means for determining a set of relationships between the received environmental data and the received feedback data, the received physiological data, or both, means for generating a message for the user based at least in part on the set of relationships, wherein the message comprises instructions for regulating the physical state of the user, the psychological state of the user, or both, when experiencing the at least one characteristic of the environment, and means for causing a GUI of a user device to display the message for the user.

A non-transitory computer-readable medium storing code is described. The code may include instructions executable by a processor to receive physiological data associated with a user from a wearable device, receive environmental data comprising at least one characteristic of an environment of the user, receive feedback data from the user indicating a physical state or a psychological state of the user when experiencing the at least one characteristic of the environment, determine a set of relationships between the received environmental data and the received feedback data, the received physiological data, or both, generate a message for the user based at least in part on the set of relationships, wherein the message comprises instructions for regulating the physical state of the user, the psychological state of the user, or both, when experiencing the at least one characteristic of the environment, and cause a GUI of a user device to display the message for the user.

Some examples of the method, apparatuses, and non-transitory computer-readable medium described herein may further include operations, features, means, or instructions for detecting the at least one characteristic of the environment within a threshold duration and generating, in response to detecting the at least one characteristic of the environment within the threshold duration, the message for the user.

Some examples of the method, apparatuses, and non-transitory computer-readable medium described herein may further include operations, features, means, or instructions for determining a trend over a duration based at least in part on of the set of relationships between the received environmental data and the received feedback data, the received physiological data, or both and wherein causing the GUI of the user device to display the message for the user may be based at least in part on the determined trend over the duration.

Some examples of the method, apparatuses, and non-transitory computer-readable medium described herein may further include operations, features, means, or instructions for determining a recurrency of at least one relationship of the set of relationships between the received environmental data and the received feedback data, the received physiological data, or both and wherein causing the GUI of the user device to display the message for the user may be based at least in part on the recurrency of the at least one relationship of the set of relationships.

Some examples of the method, apparatuses, and non-transitory computer-readable medium described herein may further include operations, features, means, or instructions for determining that the recurrency of the at least one relationship of the set of relationships between the received environmental data and the received feedback data, the received physiological data, or both, satisfies a threshold and wherein causing the GUI of the user device to display the message for the user may be based at least in part on the recurrency of the at least one relationship satisfying the threshold.

Some examples of the method, apparatuses, and non-transitory computer-readable medium described herein may further include operations, features, means, or instructions for identifying at least one estimated characteristic of the environment based at least in part on the received environmental data and wherein causing the GUI of the user device to display the message for the user may be based at least in part on the at least one estimated characteristic of the environment.

Some examples of the method, apparatuses, and non-transitory computer-readable medium described herein may further include operations, features, means, or instructions for determining a recommended action to preempt a physiological response of the user or remediate the physiological response of the user, or both, based at least in part on the at least one estimated characteristic of the environment, the physiological response corresponding to the physical state of the user, the psychological state of the user, or both, wherein the message comprises the recommended action.

In some examples of the method, apparatuses, and non-transitory computer-readable medium described herein, the at least one characteristic of the environment comprise a temperature value, a noise value, an ambient light value, an air pressure value, a humidity value, an air quality value, or any combination thereof.

In some examples of the method, apparatuses, and non-transitory computer-readable medium described herein, the feedback data comprises classifier data indicating the psychological state of the user.

In some examples of the method, apparatuses, and non-transitory computer-readable medium described herein, the classifier data comprises a contextual tag.

In some examples of the method, apparatuses, and non-transitory computer-readable medium described herein, receiving the environmental data may include operations, features, means, or instructions for receiving the environmental data via one or more applications executable on the user device, the one or more applications comprising a lifestyle application, a social media application, a utility application, an information outlet application, or any combination thereof.

In some examples of the method, apparatuses, and non-transitory computer-readable medium described herein, the wearable device comprises a wearable ring device.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method performed on a first application running on an operating system of a user device and associated with a wearable device, comprising:

receiving, at the first application, physiological data measured from a user by the wearable device, wherein the physiological data is compressed based at least in part on an elapsed time since the first application last received data from the wearable device;

receiving, from a second application running on the operating system of the user device, environmental data comprising at least one characteristic of an environment of the user;

causing a graphical user interface of the user device to display a set of user selectable tags based at least in part on each user selectable tag in the set of user selectable tags being associated with a recurring relationship between a physical state or a psychological state associated with the user selectable tag and the at least one characteristic of the environment of the user;

receiving, based at least in part on selection of one or more user selectable tags from the set of user selectable tags, feedback data from the user indicating the physical state or the psychological state of the user when experiencing the at least one characteristic of the environment;

determining, by the first application that is configured for processing data, a set of relationships correlating the received environmental data to the received feedback data, the received physiological data, or both;

generating, by the first application, a message for the user based at least in part on the set of relationships, wherein the message comprises instructions for regulating the physical state of the user, the psychological state of the user, or both, when experiencing the at least one characteristic of the environment; and causing the graphical user interface of the user device to display the message for the user.

2. The method of claim 1, further comprising:

detecting the at least one characteristic of the environment within a threshold duration; and generating, in response to detecting the at least one characteristic of the environment within the threshold duration, the message for the user.

3. The method of claim 1, further comprising:

determining a trend over a duration based at least in part on of the set of relationships between the received environmental data and the received feedback data, the received physiological data, or both, wherein causing the graphical user interface of the user device to display the message for the user is based at least in part on the determined trend over the duration.

4. The method of claim 1, further comprising:

determining a recurrency of at least one relationship of the set of relationships between the received environmental data and the received feedback data, the received physiological data, or both, wherein causing the graphical user interface of the user device to display the message for the user is based at least in part on the recurrency of the at least one relationship of the set of relationships.

5. The method of claim 4, further comprising:

determining that the recurrency of the at least one relationship of the set of relationships between the received environmental data and the received feedback data, the received physiological data, or both, satisfies a threshold, wherein causing the graphical user interface of the user device to display the message for the user is based at least in part on the recurrency of the at least one relationship satisfying the threshold.

6. The method of claim 1, further comprising:

identifying at least one estimated characteristic of the environment based at least in part on the received environmental data, wherein causing the graphical user interface of the user device to display the message for the user is based at least in part on the at least one estimated characteristic of the environment.

7. The method of claim 6, further comprising:

determining a suggested action to preempt a physiological response of the user or remediate the physiological response of the user, or both, based at least in part on the at least one estimated characteristic of the environment, the physiological response corresponding to the physical state of the user, the psychological state of the user, or both, wherein the message comprises the suggested action.

8. The method of claim 1, further comprising:

determining a suggested content based at least in part on a respective effectiveness of the at least one characteristic of the environment on the physical state of the user, the psychological state of the user, or both, wherein the message comprises the suggested content, and wherein the suggested content comprises audio content, video content, textual content, or any combination thereof.

9. The method of claim 1, wherein the at least one characteristic of the environment comprise a temperature value, a noise value, an ambient light value, an air pressure value, a humidity value, an air quality value, or any combination thereof.

10. The method of claim 1, wherein the feedback data comprises classifier data indicating the psychological state of the user.

11. The method of claim 10, wherein the classifier data comprises a contextual tag.

12. The method of claim 1, wherein receiving the environmental data comprises:

receiving the environmental data via one or more applications executable on the user device, the one or more applications comprising a lifestyle application, a social media application, a utility application, an information outlet application, or any combination thereof.

13. The method of claim 1, wherein the wearable device comprises a wearable ring device.

14. An apparatus, comprising:

one or more processors;

memory coupled with the one or more processors; and instructions stored in the memory and executable by the one or more processors to cause the apparatus to:

receive, at a first application executable by the one or more processors, physiological data measured from a user by a wearable device, wherein the physiological data is compressed based at least in part on an elapsed time since the first application last received data from the wearable device;

receive, from a second application executable by the one or more processors, environmental data comprising at least one characteristic of an environment of the user;

cause a graphical user interface of a user device to display a set of user selectable tags based at least in part on each user selectable tag in the set of user selectable tags being associated with a recurring relationship between a physical state or a psychological state associated with the user selectable tag and the at least one characteristic of the environment of the user;

receive, based at least in part on selection of one or more user selectable tags from the set of user selectable tags, feedback data from the user indicating the physical state or the psychological state of the user when experiencing the at least one characteristic of the environment;

determine, by the first application, a set of relationships between the received environmental data and the received feedback data, the received physiological data, or both;

generate, by the first application, a message for the user based at least in part on the set of relationships, wherein the message comprises instructions for regulating the physical state of the user, the psychological state of the user, or both, when experiencing the at least one characteristic of the environment; and cause the graphical user interface of the user device to display the message for the user.

15. The apparatus of claim 14, wherein the instructions are further executable by the one or more processors to cause the apparatus to:

detect the at least one characteristic of the environment within a threshold duration; and generate, in response to detecting the at least one characteristic of the environment within the threshold duration, the message for the user.

16. The apparatus of claim 14, wherein the instructions are further executable by the one or more processors to cause the apparatus to:

determine a trend over a duration based at least in part on of the set of relationships between the received environmental data and the received feedback data, the received physiological data, or both, wherein cause the graphical user interface of the user device to display the message for the user is based at least in part on the determined trend over the duration.

17. The apparatus of claim 14, wherein the instructions are further executable by the one or more processors to cause the apparatus to:

determine a recurrency of at least one relationship of the set of relationships between the received environmental data and the received feedback data, the received physiological data, or both, wherein cause the graphical user interface of the user device to display the message for the user is based at least in part on the recurrency of the at least one relationship of the set of relationships.

18. The apparatus of claim 17, wherein the instructions are further executable by the one or more processors to cause the apparatus to:

determine that the recurrency of the at least one relationship of the set of relationships between the received environmental data and the received feedback data, the received physiological data, or both, satisfies a threshold, wherein cause the graphical user interface of the user device to display the message for the user is based at least in part on the recurrency of the at least one relationship satisfying the threshold.

19. The apparatus of claim 14, wherein the instructions are further executable by the one or more processors to cause the apparatus to:

identify at least one estimated characteristic of the environment based at least in part on the received environmental data, wherein cause the graphical user interface of the user device to display the message for the user is based at least in part on the at least one estimated characteristic of the environment.

20. A non-transitory computer-readable medium storing code, the code comprising instructions executable by a processor to:

receive, at a first application executable by the processor, physiological data measured from a user by a wearable device, wherein the physiological data is compressed based at least in part on an elapsed time since the first application last received data from the wearable device;

receive, from a second application executable by the processor, environmental data comprising at least one characteristic of an environment of the user;

cause a graphical user interface of a user device to display a set of user selectable tags based at least in part on each user selectable tag in the set of user selectable tags being associated with a recurring relationship between a physical state or a psychological state associated with the user selectable tag the at least one characteristic of the environment of the user;

receive, based at least in part on selection of one or more user selectable tags from the set of user selectable tags, feedback data from the user indicating the physical state or the psychological state of the user when experiencing the at least one characteristic of the environment;

determine, by the first application, a set of relationships between the received environmental data and the received feedback data, the received physiological data, or both;

generate, by the first application, a message for the user based at least in part on the set of relationships, wherein the message comprises instructions for regulating the physical state of the user, the psychological state of the user, or both, when experiencing the at least one characteristic of the environment; and cause the graphical user interface of the user device to display the message for the user.

* * * * *